United States Patent
Caron et al.

(10) Patent No.: US 6,992,211 B2
(45) Date of Patent: Jan. 31, 2006

(54) CRYSTALLINE FORM OF PHENYLETHANOLAMINE, THE PREPARATION THEREOF AND PHARMACEUTICAL COMPOSITIONS COMPRISING THE SAME

(75) Inventors: Antoine Caron, Montbazin (FR); Olivier Monnier, Villeveyrac (FR); Sabrina Obert, Sommieres (FR); Jérome Roche, Prades le Lez (FR); Isabelle Ziri, Montpellier (FR)

(73) Assignee: Sanofi-Aventis, Paris (FR)

( * ) Notice: Subject to any disclaimer, the term of this patent is extended or adjusted under 35 U.S.C. 154(b) by 10 days.

(21) Appl. No.: 10/480,427

(22) PCT Filed: Jun. 27, 2002

(86) PCT No.: PCT/FR02/02235

§ 371 (c)(1),
(2), (4) Date: May 3, 2004

(87) PCT Pub. No.: WO03/002510

PCT Pub. Date: Jan. 9, 2003

(65) Prior Publication Data

US 2004/0180953 A1 Sep. 16, 2004

(30) Foreign Application Priority Data

Jun. 28, 2001 (FR) .................................. 01 08562

(51) Int. Cl.
*C07C 69/025* (2006.01)
*C07C 69/02* (2006.01)
*C07C 69/03* (2006.01)
*C07C 69/035* (2006.01)

(52) U.S. Cl. ..................................................... 560/231
(58) Field of Classification Search ................. 560/231
See application file for complete search history.

(56) References Cited

U.S. PATENT DOCUMENTS

| 5,202,466 A | 4/1993 | Boigegrain et al. |
| 5,270,341 A | 12/1993 | Keane et al. |

FOREIGN PATENT DOCUMENTS

| EP | 0303546 | 2/1989 |
| EP | 0489640 | 6/1992 |
| EP | 0489640 | * 10/1992 |

OTHER PUBLICATIONS

Cecchi, R. et al., Eur. J. Med. Chem., vol. 29, pp. 259-267 (1994).

* cited by examiner

*Primary Examiner*—Elvis O. Price
(74) *Attorney, Agent, or Firm*—Balaram Gupta

(57) ABSTRACT

The subject-matter of the invention is the B form of ethyl [(7S)-7-[(2R)-2-(3-chlorophenyl)-2-hydroxyethylamino]-5,6,7,8-tetrahydronaphth-2-yloxy]acetate hydrochloride, of use as a medicament, which exhibits in particular the following physical characteristics:
  characteristic IR absorption peaks ($cm^{-1}$): 2780, 2736, 1722, 1211;
  melting point: 129+/−2° C.;
  characteristic lines of the powder X-ray diffraction diagram (to within 0.1(2θ)): 7.69, 9.83, 13.95, 16.58, 18.70, 20.40, 21.57, 23.40, 24.15 and 25.64.

Figure 1:
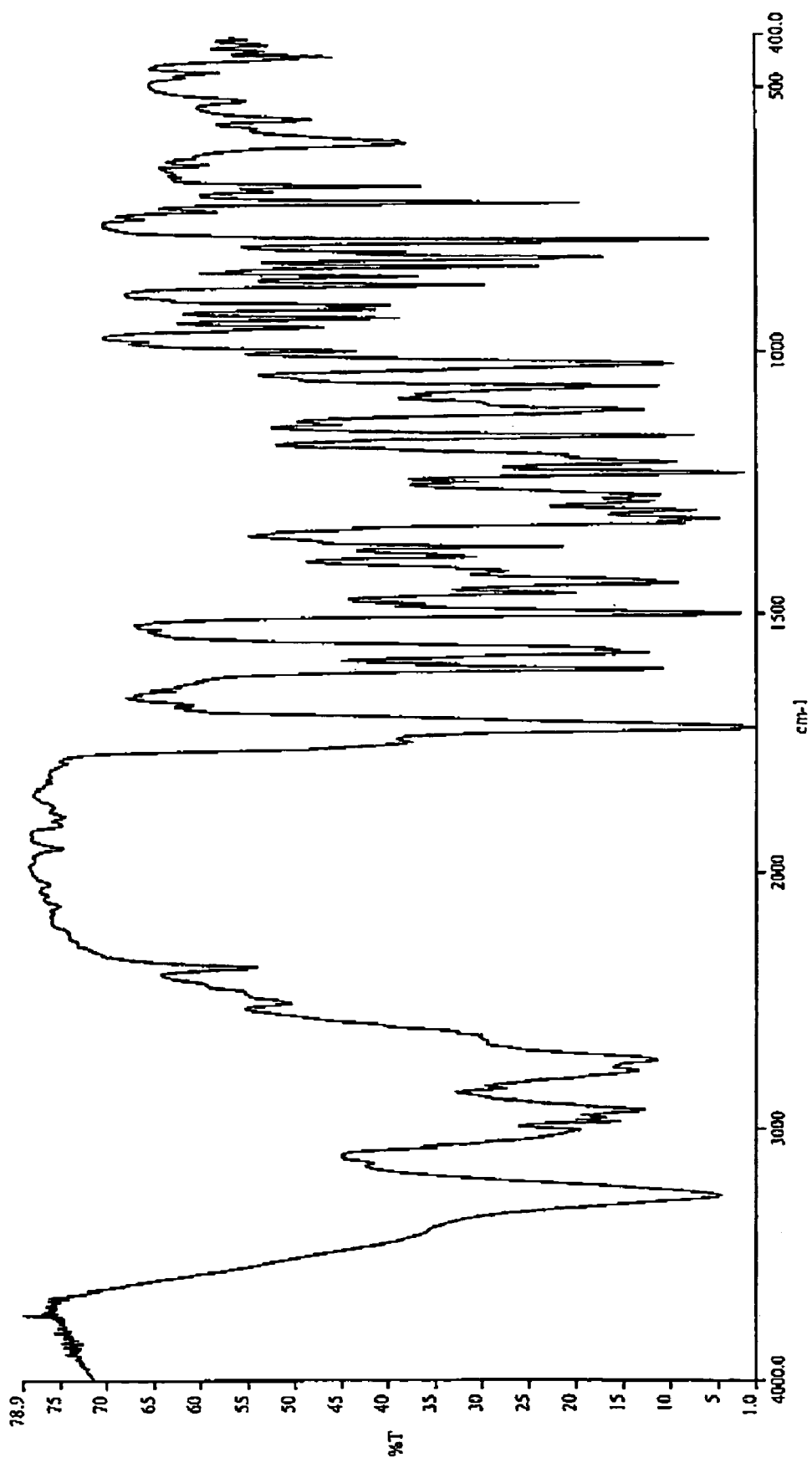

The product can be obtained by salification of the base or recrystallization of the salt from an alcohol.

27 Claims, 2 Drawing Sheets

CRYSTALLINE FORM OF PHENYLETHANOLAMINE, THE PREPARATION THEREOF AND PHARMACEUTICAL COMPOSITIONS COMPRISING THE SAME

The subject-matter of the present invention is a new crystalline form, referred to hereinbelow as B form, of ethyl [(7S)-7-[(2R)-2-(3-chlorophenyl)-2-hydroxyethylamino]-5,6,7,8-tetrahydronaphth-2-yloxy]-acetate hydrochloride, its preparation and the pharmaceutical compositions which comprise it.

This compound, also referred to according to a former nomenclature as N-[(2S)-7-ethoxycarbonylmethoxy-1,2,3,4-tetrahydronaphth-2-yl]-(2R)-(3-chlorophenyl)-2-hydroxyethanamine hydrochloride and known as SR 58611A, its preparation and its activity with respect to intestinal motricity were disclosed in EP 303546, Example 12. Subsequently, it was shown that this compound has an exceptional activity with respect to the central nervous system, making it possible to envisage its use as antidepressant (EP 0489640).

It has now been found that this compound exists in three polymorphic forms, I, II and III, known hereinbelow respectively as A form, B form and C form, one of which, referred to as B form, exhibits advantageous physical properties for the preparation of a medicament on an industrial scale.

The compound SR 58611A is described in Example 12 of EP 0303546 as a glassy solid (undetermined melting temperature) having an optical rotation of −72.9° (c=0.5%, methanol), with 4 values of the $^1$H NMR shift and 3 characteristic IR peaks. This compound, as was found subsequently, is a mixture of the three polymorphs A, B and C, with probably a majority of the A form since the absorption peak at 1203 cm$^{-1}$ indicated is specific to it (in fact 1206 cm$^{-1}$, according to a more precise measurement).

The three polymorphic forms A, B and C of the compound known as SR 58611A can now be clearly distinguished:

Melting points determined by differential scanning calorimetry (DSC):
A form (or I form): M.p. =158+/−2° C.
B form (or II form): M.p. =129+/−2° C.
C form (or III form): M.p. =120+/−2° C.
Infrared spectra, characteristic absorption peaks:
A form: 2816 cm$^{-1}$, 2740 cm$^{-1}$, 1745 cm$^{-1}$, 1206 cm$^{-1}$;
B form: 2780 cm$^{-1}$, 2736 cm$^{-1}$, 1722 cm$^{-1}$, 1211 cm$^{-1}$;
C form: 2801 cm$^{-1}$, 2750 cm$^{-1}$, 1760 cm$^{-1}$, 1200 cm$^{-1}$.
Likewise, the powder X-ray diffraction diagrams of each form are specific.

Thus, the subject-matter of the present invention is the B form of ethyl [(7S)-7-[(2R)-2-(3-chlorophenyl)-2-hydroxyethylamino]- 5,6,7,8-tetrahydronaphth-2-yloxy]acetate hydrochloride, which exhibits in particular the following physical characteristics:
characteristic IR absorption peaks (cm$^{-1}$): 2780, 2736, 1722, 1211;
melting point: 129+/−2° C.;
characteristic lines of the powder X-ray diffraction diagram (to within 0.1(2θ)): 7.69, 9.83, 13.95, 16.58, 18.70, 20.40, 21.57, 23.40, 24.15 and 25.64.

Figure 2:
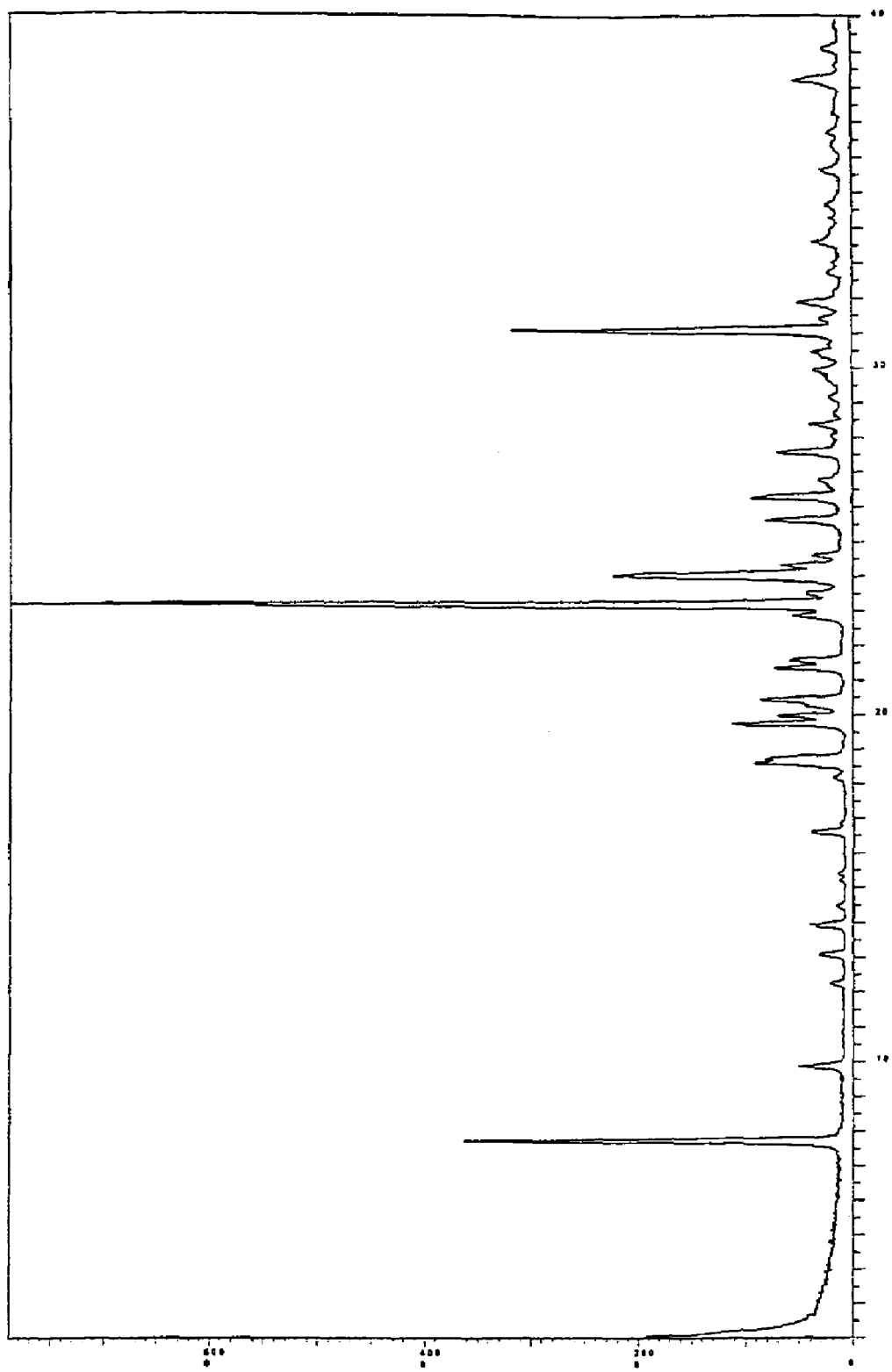

The compound is more particularly characterized with respect to the appended FIGS. 1 and 2:
FIG. 1 represents the infrared spectrum of the compound of B form according to the invention; and
FIG. 2 represents the powder X diffraction diagram of the compound of B form (obtained with a Cu Kα 1 source in a θ/θ configuration, rear monochromator)

In the present description and the claims, the term "B form of SR 58611A" or "compound of the invention" is understood to mean a product comprising at least 95% by weight and preferably at least 99% by weight of B form compared to the other polymorphs. According to a preferred aspect, a subject-matter of the invention is the B form essentially free from the other polymorphic forms according to current analytical methods.

The invention also comprises a process for the preparation of the compound according to the invention, characterized in that a solution of concentrated HCl is added to a solution of ethyl [(7S)-7-[(2R)-2-(3-chlorophenyl)-2-hydroxyethylamino]-5,6,7,8-tetrahydronaphth-2-yloxy]acetate in a solvent chosen from propan-2-ol, 2-methylpropan-2-ol and butan-2-ol at a temperature ranging from 40 to 70° C., crystallization is initiated by seeding with a small amount of the B form and then the solution is gradually cooled.

The crystallization is preferably carried out at a temperature of 50 to 70° C.

Preferably, the said solvent is propan-2-ol.

The concentrated hydrochloric acid can be commercial hydrochloric acid generally with a content of 35 to 38% by weight.

The compound of the invention can also be prepared by a recrystallization process, characterized in that ethyl [(7S)-7-[(2R)-2-(3-chlorophenyl)-2-hydroxyethylamino]-5,6,7,8-tetrahydronaphth-2-yloxy]acetate hydrochloride, in the crude form or in the form of a mixture of crystalline forms, is suspended in propan-2-ol, 2-methylpropan-2-ol or butan-2-ol at a temperature ranging from ambient temperature to 70° C. and the suspension is maintained under isothermal conditions until the crystals have been converted to the B form.

The recrystallization is advantageously carried out by initiating with a small amount of B form in order to bring about the desired specific nucleation. If no initiator is available, it is, however, possible to spontaneously obtain the conversion to B form by maintaining the other crystalline forms or the mixtures in suspension, in particular in an alcohol such as mentioned above, for a sufficient time which depends on the temperature, in particular between ambient temperature and below the boiling temperature of the alcohol.

According to another alternative form, the product of the invention can be prepared by heating a solution of ethyl [(7S)-7-[(2R)-2-(3-chlorophenyl)-2-hydroxyethylamino]-5,6,7,8-tetrahydronaphth-2-yloxy]acetate hydrochloride in an organic solvent, such as an alcohol or a ketone, to a temperature of 45 to 70° C., concentrating the solution by evaporation or distillation and then gradually cooling the solution with stirring to a temperature of 10 to 40° C.

In fact, it turned out, unexpectedly, that the B form is the most thermodynamically stable form at room temperature or more generally at a temperature of less than or equal to 70° C., as the other A and C forms or their mixtures end up by being converted to the B form when they are maintained in solution or suspension at a certain temperature for a sufficiently long time (see Examples 3 and 4), whatever the solvent. Furthermore, in addition to the possibility of having a purer and more homogeneous product, the B form can be obtained with better production efficiency, both with regard to crystallization and with regard to filtration and drying, in particular when it is prepared in propan-2-ol.

EXAMPLE 1

Preparation of the B Form of SR58611 Hydrochloride (SR58611A)

1 equivalent of concentrated hydrochloric acid is added to a propan-2-ol solution of SR58611 base (obtained according to EP 0303546) at a concentration of 100 g/l at ambient temperature. The mixture is heated to 70° C. with stirring to dissolve all the seeds which may have been formed and a linear cooling gradient is applied to 50° C. (+/−2° C.). As soon as the temperature is reached, crystallization is initiated with 2% of SR58611A seed, B form. The suspension is kept stirred under isothermal conditions at this temperature for one hour and the medium is subsequently cooled by controlled cooling gradient to 20° C. to make possible a recovery of greater than 90% of the product in the B form. The product is separated from the aqueous mother liquors by filtration, washed with propan-2-ol and dried at 50° C. under reduced pressure to give hydrochloride SR58611A, B form, melting point 125–130° C. The IR spectrum is in agreement.

EXAMPLE 2

Recrystallization of SR58611 Hydrochloride (SR58611A)

SR58611 hydrochloride (200 g), a mixture of polymorphs, obtained according to EP 0303546, is dissolved in 1.6 liters of propan-2-ol at a temperature of 80° C. 2% (with respect to the mass of SR58611A introduced) of CX black activated charcoal are added and the suspension is kept stirred at 80° C. for 15 minutes. The activated charcoal is subsequently filtered off and the filtrate is concentrated by distilling off 407 volumes of propan-2-ol.

On completion of the distillation, with stirring (Impeller-P/V=120 W/m$^3$), the homogeneous mixture is cooled to 60° C. with a linear cooling gradient of −20° C./h. As soon as a temperature of 60° C. is reached, the medium is initiated with 2% (with respect to the mass of SR58611A introduced) of SR58611A, B form, in suspension in propan-2-ol.

After maintaining for 1 hour under isothermal conditions at the seeding temperature, the suspension is cooled to 20° C. with a linear cooling gradient of −10° C./h.

The product is separated by filtration, washed with propan-2-ol (1×400 ml) and dried at 50° C. under reduced pressure to give SR58611 hydrochloride of B form (190 g), melting point 125–130° C.

EXAMPLE 3

Kinetic Conversion of SR58611A Polymorphic Mixture to B Form

Polymorphic SR58611 hydrochloride (4.46 g) is suspended at ambient temperature in 0.3 liter of propan-2-ol. After maintaining for 70 h under isothermal conditions, the suspension is composed of SR58611A hydrochloride, B form, >96%. IR spectrum and X-ray diffraction are in agreement.

EXAMPLE 4

Kinetic Conversion of SR58611A Polymorphic Mixture to B Form

Polymorphic SR58611 hydrochloride (95.2 g) is suspended at 70° C. in 0.3 liter of propan-2-ol. After maintaining for 12 h 30 under isothermal conditions, the suspension is composed of SR58611 hydrochloride, B form, >98%. IR spectrum and X-ray diffraction are in agreement.

EXAMPLE 5

Industrial Preparation of SR58611A of B Form

A dry reactor purged with nitrogen is charged with 24.7 kg of SR58611A (m.p. =159° C.), a mixture of polymorphs, and 185 l of propan-2-ol and is heated to 75° C. (temperature for complete dissolution is 68° C.). 0.49 kg of CX activated charcoal and 5 l of propan-2-ol are subsequently introduced and the temperature is brought to 80° C. for 30 minutes. The contents, maintained at 75–78° C. by nitrogen pressure, are subsequently filtered, the vessel is rinsed with 7 l of solvent, the medium is maintained for a further 10 minutes at 78° C. and then it is concentrated under atmospheric pressure to a residual volume of 99 l over approx. 1 h. The medium is cooled to 60° C. (rate 0 ?4° C./min), 0.5 kg of initiator (B form) is immediately introduced with 2.5 l of propan-2-ol and the medium is maintained at 60° C. for one hour. The medium is cooled to 20° C. (rate 0.2° C./min) and then filtered, and the filtered product is washed with 25 l of propan-2-ol and dried in vacuo at 40° C. and then 70° C. until a loss in weight <0.1% is achieved. 23.04 kg of the expected product are obtained (Yd; 93.3%). The IR spectrum and X-ray diffraction are in agreement.

EXAMPLE 6

Drying Comparison

The drying, in an agitated filter drier, of a wet filtration cake of SR58611A of A form results, in less than two hours, in a change in crystalline form and in the production of a cake composed of 90% of C form. To return to the A form, it is then necessary to continue the drying at a temperature of greater than 60° C. with agitation for approximately 48 h.

The B form exhibits the advantage of not changing crystalline form on drying. Furthermore, the shape of the crystals obtained (thick hexagonal plates) makes it possible to reduce the residual moisture content of the filtration cake to contents of less than 20% and in fact facilitates the drying of the product for the purpose of its use as medicamental active principle.

EXAMPLE 7

Pharmaceutical Composition

The product according to the invention can be administered for the treatment of depression at a dose ranging from 100 to 800 mg/day (calculated as base), in particular 300 to 600 mg/day, orally, depending on the seriousness of the complaint and the weight of the patient.

Typical formulations are tablets, including sugar-coated tablets, or gelatin capsules. Examples of gelatin capsules comprising doses of 100 and 200 mg of active principle (as base, corresponding respectively to 109.0 and 218.0 mg of hydrochloride):

| | | |
|---|---|---|
| SR58611A, B form | 100 | 200 |
| Lactose monohydrate | 330.5 (q.s.) | 217.3 |
| Hydroxypropylmethylcellulose | 4.2 | 8.4 |
| Magnesium stearate | 6.3 | 6.3 |
| Total (mg) | 450 | 450 |

What is claimed is:

1. B form of ethyl [(7S)-7-[(2R)-2-(3-chlorophenyl)-2-hydroxyethylamino]-5,6,7,8-tetrahydronaphth-2-yloxy]acetate hydrochloride, the infrared spectrum of which exhibits the following characteristic absorption peaks: 2780, 2736, 1722, 1211 cm$^{-1}$.

2. B form of ethyl [(7S)-7-[(2R)-2-(3-chlorophenyl)-2-hydroxyethylamino]-5,6,7,8-tetrahydronaphth-2-yloxy]acetate hydrochloride according to claim 1 having a melting point of 129+/−2° C., determined by differential scanning calorimetry.

3. B form of ethyl [(7S)-7-[(2R)-2-(3-chlorophenyl)-2-hydroxyethylamino]-5,6,7,8-tetrahydronaphth-2-yloxy]acetate hydrochloride according to claim 1, the powder X-ray diffraction diagram of which exhibits the following characteristic lines: 7.69, 9.83, 13.95, 16.58, 18.70, 20.40, 21.57, 23.40, 24.15 and 25.64.

4. Process for the preparation of the compound according to claim 1 wherein a solution of concentrated HCl is added to a solution of ethyl [(7S)-7-[(2R)-2-(3-chlorophenyl)-2-hydroxyethylamino]-5,6,7,8-tetrahydronaphth-2-yloxy]acetate in a solvent chosen from propan-2-ol, 2-methylpropan-2-ol and butan-2-ol at a temperature ranging from 40 to 70° C., crystallization is initiated by seeding with a small amount of the B form and then the solution is gradually cooled.

5. Process according to claim 4 wherein the crystallization is carried out at a temperature of 50 to 70° C.

6. Process according to claim 4 wherein the solvent is propan-2-ol.

7. Process for the preparation of the compound according to claim 1 wherein ethyl [(7S)-7-[(2R)-2-(3-chlorophenyl)-2-hydroxyethylamino]-5,6,7,8-tetrahydronaphth-2-yloxy]acetate hydrochloride is suspended in propan-2-ol, 2-methylpropan-2-ol and butan-2-ol at a temperature ranging from ambient temperature to 70° C. and the suspension is maintained under isothermal conditions until the crystals have been converted to the B form.

8. Process for the preparation of the compound according to claim 1 wherein a solution of ethyl [(7S)-7-[(2R)-2-(3-chlorophenyl)-2-hydroxyethylamino]-5,6,7,8-tetrahydronaphth-2-yloxy]acetate hydrochloride in an organic solvent chosen from an alcohol or a ketone is heated to a temperature of 45 to 70° C., the solution is concentrated by evaporation or distillation and then the solution is gradually cooled with stirring to a temperature of 10 to 40° C.

9. Process according to claim 8 wherein the solvent is propan-2-ol.

10. Pharmaceutical composition, comprising the compound according to claim 1 as active principle and one or more pharmaceutically acceptable excipients.

11. Process for the preparation of the compound according to claim 2 wherein a solution of concentrated HCl is added to a solution of ethyl [(7S)-7-[(2R)-2-(3-chlorophenyl)-2-hydroxyethylamino]-5,6,7,8-tetrahydronaphth-2-yloxy]acetate in a solvent chosen from propan-2-ol, 2-methylpropan-2-ol and butan-2-ol at a temperature ranging from 40 to 70° C., crystallization is initiated by seeding with a small amount of the B form and then the solution is gradually cooled.

12. Process for the preparation of the compound according to claim 3 wherein a solution of concentrated HCl is added to a solution of ethyl [(7S)-7-[(2R)-2-(3-chlorophenyl)-2-hydroxyethylamino]-5,6,7,8-tetrahydronaphth-2-yloxy]acetate in a solvent chosen from propan-2-ol, 2-methylpropan-2-ol and butan-2-ol at a temperature ranging from 40 to 70° C., crystallization is initiated by seeding with a small amount of the B form and then the solution is gradually cooled.

13. Process according to claim 11 wherein the crystallization is carried out at a temperature of 50 to 70° C.

14. Process according to claim 11 wherein the crystallization is carried out at a temperature of 50 to 70° C.

15. Process according to claim 11 wherein the solvent is propan-2-ol.

16. Process according to claim 12 wherein the solvent is propan-2-ol.

17. Process according to claim 5 wherein the solvent is propan-2-ol.

18. Process according to claim 13 wherein the solvent is propan-2-ol.

19. Process according to claim 14 wherein the solvent is propan-2-ol.

20. Process for the preparation of the compound according to claim 2 wherein ethyl [(7S)-7-[(2R)-2-(3-chlorophenyl)-2-hydroxyethylamino]-5,6,7,8-tetrahydronaphth-2-yloxy]acetate hydrochloride is suspended in propan-2-ol, 2-methylpropan-2-ol and butan-2-ol at a temperature ranging from ambient temperature to 70° C. and the suspension is maintained under isothermal conditions until the crystals have been converted to the B form.

21. Process for the preparation of the compound according to claim 3 wherein ethyl [(7S)-7-[(2R)-2-(3-chlorophenyl)-2-hydroxyethylamino]-5,6,7,8-tetrahydronaphth-2-yloxy]acetate hydrochloride is suspended in propan-2-ol, 2-methylpropan-2-ol and butan-2-ol at a temperature ranging from ambient temperature to 70° C. and the suspension is maintained under isothermal conditions until the crystals have been converted to the B form.

22. Process for the preparation of the compound according to claim 2 wherein a solution of ethyl [(7S)-7-[(2R)-2-(3-chlorophenyl)-2-hydroxyethylamino]-5,6,7,8-tetrahydronaphth-2-yloxy]acetate hydrochloride in an organic solvent chosen from an alcohol or a ketone is heated to a temperature of 45 to 70° C., the solution is concentrated by evaporation or distillation and then the solution is gradually cooled with stirring to a temperature of 10 to 40° C.

23. Process for the preparation of the compound according to claim 3 wherein a solution of ethyl [(7S)-7-[(2R)-2-(3-chlorophenyl)-2-hydroxyethylamino]-5,6,7,8-tetrahydronaphth-2-yloxy]acetate hydrochloride in an organic solvent chosen from an alcohol or a ketone is heated to a temperature of 45 to 70° C., the solution is concentrated by evaporation or distillation and then the solution is gradually cooled with stirring to a temperature of 10 to 40° C.

24. Process according to claim 5 wherein the solvent is propan-2-ol.

25. Process according to claim 5 wherein the solvent is propan-2-ol.

26. Pharmaceutical composition, comprising the compound according to claim 2 as active principle and one or more pharmaceutically acceptable excipients.

27. Pharmaceutical composition, comprising the compound according to claim 3 as active principle and one or more pharmaceutically acceptable excipients.

* * * * *